United States Patent [19]

Yamamoto et al.

[11] Patent Number: 5,062,990

[45] Date of Patent: Nov. 5, 1991

[54] DISCOTIC OCTASUBSTITUTED TETRAPYRAZINOTETRAAZAPORPHYRAZINES

[75] Inventors: Iwawo Yamamoto, No 16-25, 2-chome, Fumiiri, Ueta City, Nagano Pref.; Kazuchika Ohta, Ueda, both of Japan

[73] Assignees: Eastern Co., Ltd., Chino; Iwawo Yamamoto, Ueda, both of Japan; a part interest

[21] Appl. No.: 457,397

[22] Filed: Dec. 27, 1989

[30] Foreign Application Priority Data

Feb. 17, 1989 [JP] Japan ..................... 1-36018

[51] Int. Cl.$^5$ ..................... C09K 19/34; C09K 19/58; C07D 487/22
[52] U.S. Cl. ..................... 252/299.61; 252/299.01; 252/299.6; 252/299.3; 252/299.2; 540/121
[58] Field of Search ..................... 540/121; 252/299.01, 252/299.6, 299.61, 299.3, 299.2

[56] References Cited

U.S. PATENT DOCUMENTS

| | | | |
|---|---|---|---|
| 3,058,991 | 10/1962 | Wolf et al. | 540/121 |
| 3,063,779 | 11/1962 | Rösch et al. | 540/121 |
| 3,509,146 | 4/1970 | Weinberger et al. | 540/121 |
| 3,923,645 | 12/1975 | Anderson, Jr. et al. | 540/121 |
| 4,647,478 | 3/1987 | Formanek et al. | 252/299.1 X |
| 4,657,554 | 4/1987 | Reinert et al. | 540/121 |
| 4,960,538 | 10/1990 | Itoh et al. | 252/299.2 |

FOREIGN PATENT DOCUMENTS

| | | | |
|---|---|---|---|
| 754503 | 10/1970 | Belgium | 540/121 |
| 1132300 | 12/1984 | U.S.S.R. | 540/121 |

*Primary Examiner*—John S. Maples
*Assistant Examiner*—Richard Treanor
*Attorney, Agent, or Firm*—Dilworth & Barrese

[57] ABSTRACT

Octasubstituted tetraphyrazinotetraazaporphrazine and compositions forming an electron acceptable discotic liquid crystal phase are disclosed. Said compounds and the metal complexes are easily soluble in an organic solvent such as chloroform or dichloromethane etc and are insoluble in acetone and alcohols; and therefore a columnar phase by silica gel/dichloromethane, recrystallization from tetra-hydrofuran or refining through solid liquid extraction by acetone is possible. Furthermore, stability in a giant molecular can be expected and a functional membrane can be formed by a solution cast method etc., thereby employing as an electon or photoelectron material or an indication element.

14 Claims, 1 Drawing Sheet

DISCOTIC OCTASUBSTITUTED TETRAPYRAZINOTETRAAZAPORPHYRAZINES

BACKGROUND OF THE INVENTION

The present invention relates to octasubstituted tetrapyrazinotetraazaporphyrazines which are soluble in an organic solvent and the compounds having an electron acceptable discotic liquid crystal phase.

Hitherto, phthalocyanine compounds have been known as a pigment or a functional material. The compounds may be synthesized with comparative ease, however on the other hand, almost of said compounds are insoluble in a solvent and accordingly are difficult to purify and use. Furthermore, said compounds are expected to be available for electric conductive organic compounds. The formation of CT complex by mixing dopes or electron acceptors therewith has been attempted in order to induce electric conductivity under consideration of the properties of electron donor and conductivity. However, there was a problem in the stability thereof.

SUMMARY OF THE INVENTION

With the above in mind, it is an object of the present invention to provide novel compounds in order to resolve such conventional drawbacks as difficulties in the purification and application of phthalocyanine compounds and further improve the stability of ct complex by mixing dopes or electron acceptors with said compounds.

The aforementioned object of the present invention can be attained by providing novel compounds (1a) and the metal complex compounds (1b) thereof having the following general formula:

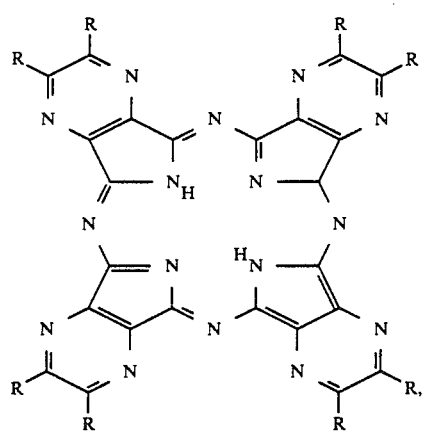

(1a)

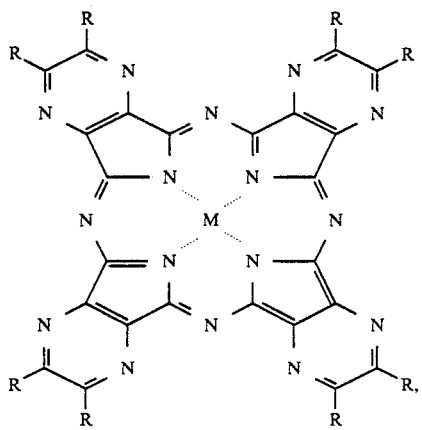

(1b)

wherein R represents aliphatic alkyl of 1-20 carbons and M represents a metal atom.

Among tetrapyrazinotetraazaporphyrazines, the present invention relates to tetrapyrazinotetraazaporphyrazines (1a) having substituted positions of 5,6,5',6',5'',6'',5''' and 6'''0 aliphatic alkyl and the metal complex compounds (1b) thereof having the aforementioned general formula, wherein R represents aliphatic alkyl, being a normal aliphatic alkyl base of 1-20 carbons, preferably 6-12 carbons for solubility and mesomorphism and M represents a metal atom such as copper, zinc, lead, iron, cobalt or nickel, preferably copper or zinc.

DESCRIPTION OF THE PREFERRED EMBODIMENTS

Figure 1A:
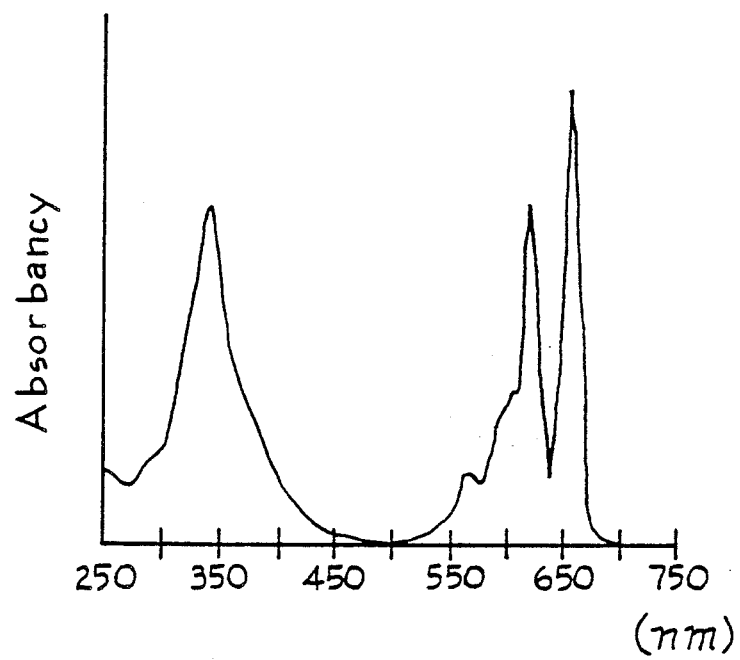
FIG. 1(a) is ultraviolet-visible absorption spectrum of the compound (1a-1) according to the present invention.

Hereinafter, embodiments according to the present invention will be described in detail with reference to the drawings.

The compounds (1a) and the metal complex compounds (1b) thereof according to the present invention can be prepared through the following process; in detail,

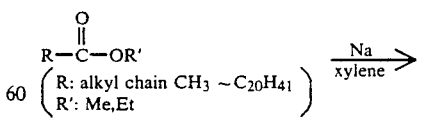

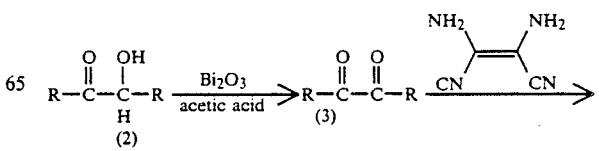

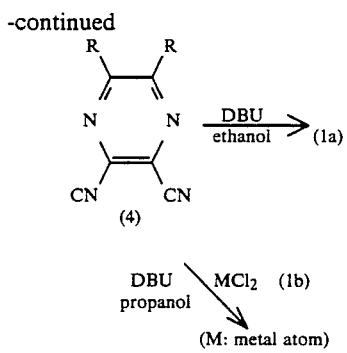

In detail, aliphatic carboxylic acid ester is subjected to acyloin type condensation and α-hydroxyketone (2) thus obtained is oxidated by bismuth oxide so as to obtain α-diketone (3). After dehydrating reaction of said α-diketone (3) and diaminomaleonitrile, dicyanopyridine derivatives (4) are obtained and then the compounds (1a) are obtained under reaction of said derivatives (4) in the presence of a base. Further, the metal complex compound (1b) is obtained under the reaction of metal chloride in the presence of a base.

EXAMPLE 1

Synthesis of octasubstituted tetrapyrazinotetraazaporphyrazine (1a-1), wherein R is 12 carbons 0.38 mole of metal sodium are added into 300 ml of absolute xylene to be dispersed under heating. Thereafter, 0.19 mole of tri-decanoic methylate are added thereto for one hour reaction. Separating α-hydroxyketone (yield 63%) thus produced, $5.8 \times 10^{-2}$ mole of this compound is circulated under heating with $7.0 \times 10^{-2}$ mole of bismuth oxide in acetic acid so as to oxidize said compound. After separating α-diketone (yield 67%) thus produced, $3.8 \times 10^{-2}$ mole of said α-diketone and $9.5 \times 10^{-2}$ mole of diaminomaleonitrile are circulated under heating in acetic acid for 12 hours so as to obtain 2,3-dicyano-5,6-didodecylpyrazine (yield 85%). $4.55 \times 10^{31\ 3}$ mole of said 2,3-dicyano-5,6-didodecylpyrazine are circulated under heating in absolute alcohol for 12 hours in the presence of 1,8-diazabicyclo (5,4,0)-7-undecene (abbreviation DBU) so as to obtain the compound (1a-1).

As a result of element analysis, hydrogen was 10.84% (calculated value 10.89%), carbon was 77.06% (calculated value 77.12%) and nitrogen was 11.97% (calculated value 11.99%).

As a result of ultraviolet-visible spectroscopy, characteristic absorption of tetrapyrazinotetraazaporphyrazines was observed at 618 nm and 654 nm as shown in FIG. 1(a).

Furthermore, the compound (1a-1) thus produced showed low temperature crystallization (solid phase-solid phase transition temperature 94° C.) and high temperature crystallization (melting point 118° C.) and further showed discotic liquid crystal phase at 118° C. and above the phase decomposed at 238° C. and above. Table 1 shows each transition temperature and entropy change. The half-step potential of cyclic voltammetry is −0.50 V, showing the characteristic of an electron acceptor.

The compound (1a-1) was easily soluble in chloroform and dichloromethane.

TABLE 1

| Compound | Phase transmition temperature entropy change Ht(Kcal/mole) |
| --- | --- |
| tetrapyrazinotetra-azaporphyrazine(1a-1) | $K_1 \xrightarrow[(6.2)]{94} K_1 \xrightarrow[(8.8)]{118} D \xrightarrow{238}$ decomposition |
| tetrapyrazinotetra-azaporphyrazine copper complex(1b-1) | $K_1 \xrightarrow[4.9]{71} K_1 \xrightarrow[(0.74)]{92} K_3 \xrightarrow[(10.2)]{114}$ $D \xrightarrow{288}$ decomposition |

(K: crystal phase D: discotic liquid crystal phase)

EXAMPLE 2

Synthesis of octasubstituted tetrapyrazinotetraazaporphyrazine metal complex (1b-1)

$6.4^3 \times 10^{-3}$ mole of 2,3-dicyano-5,6-didodecylpyrazine (in the formula 1b, R=12 carbons) and $1.77 \times 10^{-3}$ mole of copper chloride (CuCl$_2$) were reacted in the presence of DBU so as to obtain metal complex (1b-1).

As a result of element analysis of the metal complex thus obtained, hydrogen was 10.45% (calculated value 10.44%); carbon was 74.75% (calculated value 74.65%) and nitrogen was 11.38% (calculated value 11.61%).

Figure 1B:
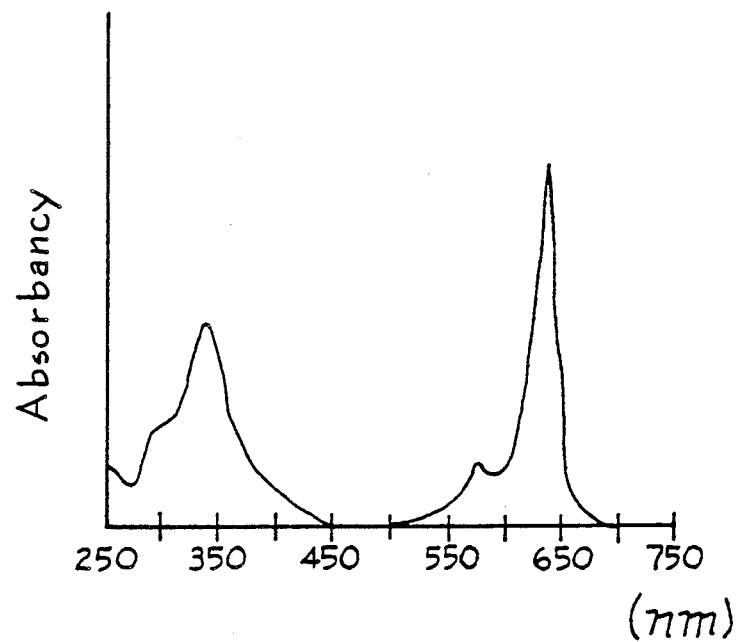
FIG. 1(b) is ultraviolet-visible absorption spectrum of the metal complex compound (1b-1) according to the present invention.

As a result of ultraviolet-visible spectroscopy, characteristics absorption of tetrapyrazinotetraazaporphyrazine metal complex was observed at 634 nm as shown in FIG. 1(b).

The metal complex (1b-1) also showed low temperature crystallization (solid phase-solid phase transition temperature 71° C.) and two high temperature crystallizations (solid phase-solid phase transition temperature 92° C. and melting point 114° C.). It also showed discotic liquid crystal phase at 114° C. and above. Further, the phase was decomposed at 288° C. and above.

Table 1 shows each transition temperature and entropy change.

The half-step potential of cyclic voltammetry was −0.40 V, showing the characteristic of an electron acceptor.

The metal complex (1b-1) is also easily soluble in chloroform and dichloromethane.

As described hereinabove, the compounds (1a) and the metal complex compounds (1b) according to the present invention are easily soluble in an organic solvent such as chloroform or dichloromethane, etc., and are insoluble in acetone and alcohols; and therefore columnar phase of said compounds (1a) and the metal complex compounds (1b) can be made by silica gel/dichloromethane and further recrystallization from tetrahydrofuran or refining through solid liquid extraction by acetone can also be made. Furthermore, since said compounds (1a) and the metal complex compounds (1b) are soluble in an organic solvent, stability in giant molecular compounds can be expected and further a functional membrane can be formed by a solution cast method etc., thereby utilizing the same as an electron or photoelectron material and an indication element.

Still furthermore, the compounds (1a) or the metal complex compounds (1b) according to the present invention may form CT complex with an electron acceptable discotic liquid crystal, thereby being available as a one-dimensional electric conductor.

What is claimed is:

1. A discotic liquid crystal phase having electron-accepting character and comprising a tetrapyrazinotetraazaporphyrazine compound of the following formulas (1a) or (1b):

(1a)

(1b)

wherein R is selected from at least one of $C_6H_{13}$, $C_7H_{15}$, $C_8H_{17}$, $C_9H_{19}$, $C_{10}H_{21}$, $C_{11}H_{23}$ and $C_{12}H_{25}$ and M is Cu, Zn, Pb, Fe, Co or Ni.

2. The discotic liquid crystal phase of claim 1 wherein R is $C_6H_{13}$.

3. The discotic liquid crystal phase of claim 1 wherein R is $C_7H_{15}$.

4. The discotic liquid crystal phase of claim 1 wherein R is $C_8H_{17}$.

5. The discotic liquid crystal phase of claim 1 wherein R is $C_9H_{19}$.

6. The discotic liquid crystal phase of claim 1 wherein R is $C_{10}H_{21}$.

7. The discotic liquid crystal phase of claim 1 wherein R is $C_{11}H_{23}$.

8. The discotic liquid crystal phase of claim 1 wherein R is $C_{12}H_{25}$.

9. The discotic liquid crystal phase of claim 1 wherein M is Cu.

10. The discotic liquid crystal phase of claim 1 wherein M is Zn.

11. The discotic liquid crystal phase of claim 1 wherein M is Pb.

12. The discotic liquid crystal phase of claim 1 wherein M is Fe.

13. The discotic liquid crystal phase of claim 1 wherein M is Co.

14. The discotic liquid crystal phase of claim 1 wherein M is Ni.

* * * * *